United States Patent [19]

Connor et al.

[11] Patent Number: 5,444,085

[45] Date of Patent: Aug. 22, 1995

[54] METHODS OF INHIBITING HIV AND INHIBITING THE ACTIVATION OF HIV

[75] Inventors: David T. Connor; Stephen J. Gracheck; Leonard Post, all of Ann Arbor, Mich.

[73] Assignee: Warner-Lambert Company, Morris Plains, N.J.

[21] Appl. No.: 358,643

[22] Filed: Dec. 19, 1994

Related U.S. Application Data

[63] Continuation of Ser. No. 106,505, Aug. 13, 1993, abandoned.

[51] Int. Cl.⁶ .............................................. A61K 31/38
[52] U.S. Cl. ...................................... 514/443; 514/448
[58] Field of Search ............................... 514/443, 448

[56] References Cited

U.S. PATENT DOCUMENTS

| | | | |
|---|---|---|---|
| 5,208,253 | 5/1993 | Boschelli et al. | 514/443 |
| 5,244,893 | 9/1993 | Elbe et al. | 514/212 |

FOREIGN PATENT DOCUMENTS 0221345  5/1987  European Pat. Off. .

OTHER PUBLICATIONS

*Agents and Actions*, vol. 34, 1991, pp. 53–55, Dong et al.
*Antiviral Chemistry & Chemotherapy*, vol. 4, No. 1, pp. 55–63, 1993.
*Journal of Virology*, vol. 65, No. 9, pp. 4645–4653, 1991.
*The Journal of Immunology*, vol. 148, No. 12, pp. 3991–3996, 1992.
*Proc. Natl. Acad. Sci. USA.* vol. 83, pp. 1911–1915, 1986.
*AIDS*, vol. 6, No. 1, pp. 3–16, 1992.
*Nature*, vol. 362, pp. 355–358, 1993.
*AIDS*, vol. 6, No. 9, pp. 991–997, 1992.
*Biochem. Biophys. Res. Comm.*, vol. 164, No. 1, pp. 339–344, 1989.
*AIDS Research and Human Retroviruses*, vol. 8, No. 6, pp. 991–995, 1992.

*Primary Examiner*—Marianne M. Cintins
*Assistant Examiner*—Russell Travers
*Attorney, Agent, or Firm*—Michael J. Atkins; Charles W. Ashbrook

[57] ABSTRACT

The present invention discloses compounds which substantially inhibit HIV or the activation of HIV in HIV-infected individuals. The compounds, their derivatives, and pharmacologic salts may be formulated into a pharmacologic agent to treat HIV infections. These pharmacologic agents may be used to treat immunosuppression, and other diseases of the immune system. The present invention also provides methods for preparing the compounds and formulating the compounds into pharmacologic agents.

21 Claims, 6 Drawing Sheets

METHODS OF INHIBITING HIV AND INHIBITING THE ACTIVATION OF HIV

This application is a continuation of Ser. No. 08/106,505, filed Aug. 13, 1993, now abandoned.

FIELD OF THE INVENTION

The present invention discloses a series of known compounds which substantially inhibit the human immunodeficiency virus (HIV) and inhibit the activation of HIV in HIV-infected individuals. In addition, the present invention provides methods of using these compounds as immunosuppressives and for the treatment of other diseases of the immune system. These compounds are also useful for the preparation of pharmaceutical compositions for use as inhibitors of HIV, inhibitors of the activation of HIV in HIV-infected individuals, as immunosuppressives, and for the treatment of other diseases of the immune system.

BACKGROUND

The pathogenesis of the human immunodeficiency virus (HIV) is complicated and as of yet not completely understood. The virus life cycle has theoretically been divided into afferent and efferent components. Virus binding, fusion, reverse transcription, and finally integration are among those events which encompass the afferent component of the life cycle. It is the afferent component of the HIV life cycle which is responsible for primary infection of HIV in an individual, generally followed by a burst of viraemia with or without clinical symptoms.

Many therapeutic strategies have been developed and targeted for intervention during the afferent events. See for example, Mitsuya H and Broder S: Inhibition of the in vitro infectivity and cytopathic effect of human T-lymphotropic virus type III/Lymphadenopathy virus-associated virus (HTLV-III/LAV) by 2', 3'-dideoxynucleosides, *Proc. Natl. Acad. Sci.* (USA) 1986;83:1911–1915.

Whereas different stages of the afferent component offer the potential for effective therapeutic intervention, it has become increasingly apparent that intervention solely at these points is insufficient. After becoming infected with HIV and the disease progresses through the afferent stages, an individual experiences a prolonged period of clinical latency which may extend for several years and the individual remains in good health. At this point in time, low to absent levels of viraemia and virus replication in peripheral blood cells are achieved. At a later point, however, the disease eventually progresses to life-threatening constellation of disease and immunosuppression (AIDS) for which there remains no cure. These later events are the clinical manifestations of the efferent stages of HIV infection.

The efferent component of the HIV life cycle includes those events necessary for the HIV provirus to successfully transcribe, translate, assemble, and produce virions. Onset of the events necessary for HIV-infected cells to progress from an asymptomatic, non-HIV expressive stage to a symptomatic, HIV expressive stage is referred to as activation. Presently, the efferent component and the cellular basis for activation is not completely understood. Nevertheless, if novel therapeutic agents and strategies are developed and implemented during the clinically asymptomatic phase to fight the progression toward AIDS, some hope may be afforded the estimated one million infected, but clinically asymptomatic individuals.

Attempts at understanding the virologic and cellular basis for the clinical asymptomatic period reveal that HIV exists as a dormant or nonexpressing provirus in a reservoir population of chronically infected cells. A specific type of HIV, HIV-1, has been the subject of a number of different research projects which have shown that the virus exists as a dormant or nonexpressing provirus in a reservoir population of chronically infected T-lymphocytic cells. Greater detail concerning the nuclear and biochemical mechanisms responsible for maintaining the nonexpressive viral state, however, is beyond the scope of this review, but can be found in detail elsewhere. Mechanisms of HIV-1 Latency, Bednarik, et al., AIDS 1992;6:3–16.

Until recently, it was believed that HIV was dormant or nonexpressing in all the reservoir population of chronically infected cells during the clinical asymptomatic period. Observations of the low to absent levels of viraemia and virus replication in peripheral blood cells led to the impression that HIV disease was not active during the clinical asymptomatic period. A team of scientists, however, have discovered that a true state of microbiological latency does not exist during the course of HIV infection. Fauci AS, et al., HIV Infection is Active and Progressive in Lymphoid Tissue During the Clinically Latent Stage of disease, Nature 1993;362:355–358.

The scientists reported a dichotomy between the levels of viral burden and virus replication in peripheral blood versus lymphoid organs during clinical latency. Based on these findings, therefore, the scientists have discovered that "peripheral blood does not accurately reflect the actual state of HIV disease, particularly early in the clinical course of HIV infection. In fact, HIV disease is active and progressive even when there is little evidence of disease activity by readily measured viral parameters in the peripheral blood, and the patient is experiencing clinical latency."

Inevitably, the disease state of HIV progresses from the clinically latent asymptomatic period to the expressive and active symptomatic period. Through the use of several different models, an understanding of the cellular pathways involved in HIV activation from laboratory latency has begun to unfold. According to Butera, et al., AIDS 1992;6:994, many of the cellular models of latency can be induced to express HIV-1 upon treatment with cytokines. This indicates that in the state of microbiologic latency, HIV-1 awaits an extracellular stimulus before initiating replication. This signal not only can be mediated though a soluble cytokine interaction with its receptor, but also through receptor-receptor interactions which occur during cell to cell communication or cellular stress such as UV light exposure and heat shock. Furthermore, an extracellular induction signal can be generated in an autocrine or paracrine fashion so that an HIV-1 activated cell can propagate its own expression while activating a nearby latent cell.

Additional factors have been considered by those of skill in the art to be involved in the activation of HIV. One study has shown that 12-O-tetradecanoyl-phorbol-13-acetate (TPA) mediates CD4 down regulation and viral expression in HIV-infected cells. Hamamoto, et al., *Biochem. Biophys. Res. Commun.* 1989;164:339–344. Interestingly, Hamamoto also examined the effect of the potent protein kinase C inhibitors staurosporine, H-7, and UCN-01 on TPA-mediated CD4 down regulation and augmentation of HIV expression. Staurosporine was found to be an effective TPA inhibitor for both of these actions.

The cellular pathways involved in mediating the activating signal from the plasma membrane to the integrated virus, resulting in HIV-1 expression, are much less clear. Recently, the development of a reliable and simple system for evaluating compounds that could prevent activation of latent HIV was reported at the National Cooperative Discovery Grant (NCDDG)/AIDS by P. Feorino, S. T. Butera, T. M. Folks, and R. F. Schinazi, San Diego, Calif., Nov. 3–7, 1991. The assay system employed the OM-10.1 cell line, a unique chronically-infected promyelocytic clone which remains CD4+ until HIV-1 activation with tumor necrosis factor-α. The expression of CD4+ on the cell surface and the activity of reverse transcriptase are used as markers for quantitating viral expression. Alternatively, other HIV markers, such as protease activity, which are known to those of skill in the art can be used. OM-10.1 cells remain CD4+ until viral activation and respond to tumor necrosis factor induction, and therefore, these cultures are used to conveniently and rapidly examine pharmacologics for an ability to prevent CD4+ down modulation (decrease in expression of CD4+ on the cell surface) and HIV-1 expression.

A variety of compounds known to have antiviral properties against either acutely or chronically infected cells were evaluated for their ability to inhibit HIV expression in these OM-10.1 cells. Several compounds that interact with biochemical pathways that may interfere with the activation process were also examined. The results of the evaluation were presented in a poster at the NCDDG/AIDS, San Diego, Calif., Nov. 3–7 (1991). Among some 48 compounds evaluated, 3'-fluoro-3'-deoxythymidine (FLT), interferon Y, and desferrioxamine were considered modest inhibitors of the activation of HIV-1.

The compounds of the present invention are known and disclosed in U.S. Pat. No. 5,208,253 issued to Boschelli, et al., on May 4, 1993. The compounds disclosed in this issued patent are useful as agents which block leukocyte adherence to vascular endothelium and, as such, are effective therapeutic agents for treating inflammatory diseases. The disclosure of this issued patent is hereby incorporated by reference.

There is no disclosure in the above-identified reference to suggest the use of the compounds identified in this present application as anti-HIV or anti-HIV activating materials, as immunosuppressives, and for the treatment of other diseases of the immune system.

SUMMARY

The present invention offers novel therapeutic strategies for the treatment of infection by the human immunodeficiency virus (HIV) and the treatment of consequent pathological conditions such as the lethal immunosuppression (AIDS) experienced by those individuals infected with the human immunodeficiency virus (HIV). Treating AIDS or treating infection by HIV is defined as including, but not limited to, treating a wide range of states of HIV infection: AIDS, ARC (AIDS related complex), both symptomatic and asymptomatic, and actual or potential further exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

It has been found that certain compounds, their derivatives, and pharmaceutically acceptable salts thereof, intervene in the eventual progression of HIV from an asymptomatic state to an active, progressive, life-threatening immunosuppressive state. While not wishing to be bound by theory, the compounds are believed to inhibit agents which activate transcription from HIV integrated within or already excised from an infected mammalian DNA. In addition, it has been found that pharmaceutical compositions comprised of the aforementioned compounds, their derivatives, and salts can intervene in the eventual progression of HIV from a clinically latent state to an active, progressive, life-threatening immunosuppressive state (AIDS or AIDS related complex). The administration of these compositions to mammals in need thereof will offer the opportunity to devise new therapies effective against acute and chronic HIV infections.

The present invention employs the newly developed physiologic tissue culture cell-based model of latency, OM-10.1, to identify therapeutic compounds for an ability to prevent HIV activation (*J. Virol.* 1991;65:4645–4653). The identified therapeutic compounds selectively block cellular pathways involved in HIV activation. The development of these therapeutic compounds into pharmacologic agents offers the prospect of a prolonged asymptomatic clinical period of latency.

BRIEF DESCRIPTION OF THE DRAWINGS

The invention is described by way of example with reference to the accompanying drawings wherein:

FIG. 1 is a graph representing the reversal of HIV-1 induction as evidenced by inhibition of Supernatant Reverse Transcriptase Activity in OM-10.1 Induction Cultures by the following compounds:

5-methoxy-3-(1-methylethoxy)benzothiophene-2-carboxamide and 5-methoxy-3-(1-methylethoxy)benzothiophene-2-carboxamide, 1-oxide.

FIG. 2 is another graph representing the reversal of HIV-1 induction as evidenced by inhibition of Supernatant Reverse Transcriptase Activity in OM-10.1 Induction Cultures by the following compounds:

5-methoxy-3-(1-methylethoxy)benzothiophene-2-carboxamide and 5-methoxy-3-(1-methylethoxy)benzothiophene-2-carboxamide-, 1-oxide.

FIG. 3 is still another graph representing the reversal of HIV-1 induction as evidenced by inhibition of Supernatant Reverse Transcriptase Activity in OM-10.1 Induction Cultures by the following compounds:

5-methoxy-3-(1-methylethoxy)benzothiophene-2-carboxamide and 5-methoxy-3-(1-methylethoxy)benzothiophene-2-carboxamide-, 1-oxide.

FIG. 4 is a graph representing the inhibition of CD4 Down-modulation in OM-10.1 Induction Cultures by the following compounds:

5-methoxy-3-(1-methylethoxy)benzothiophene-2-carboxamide and

5-methoxy-3-(1-methylethoxy)benzothiophene-2-carboxamide-, 1-oxide.

DETAILED DESCRIPTION OF THE PREFERRED EMBODIMENTS

The present invention discloses a number of compounds for use as inhibitors of HIV or inhibitors of the activation of HIV in HIV-infected individuals, as immunosuppressives, and for the treatment of other diseases of the immune system. As indicated previously, these compounds are known and their methods of preparation have been taught in U.S. Pat. No. 5,208,253 issued to Boschelli, et al., on May 4, 1993. Specifically, compounds of the present invention are of the formula (I):

wherein
$R_1$ is lower alkyl, phenyl, or benzyl;
$R_2$ is hydrogen, lower alkyl, phenyl, benzyl, thiophene, $(CH_2)_m Q$, or phenyl, benzyl, or thiophene substituted with $(CH_2)_m Q$;
n is an integer from 0 to 2;
m is an integer from 0 to 6;
Q is $CO_2 R_7$ where $R_7$ is hydrogen or lower alkyl; and
$R_3$, $R_4$, $R_5$, $R_6$ are independently hydrogen, halo, hydroxy, nitro, amino, lower alkyl, and lower alkoxy.

Lower alkyl and lower alkoxy mean a straight or branched alkyl or alkoxy group having one to four carbon atoms and includes, for example, methyl, ethyl, propyl, i-propyl, or otherwise referred to as (methyl-)ethyl, and t-butyl or otherwise referred to as 1,1-(dimethyl)ethyl, and correspondingly, for example, methoxy, ethoxy, i-propoxy or otherwise referred to as 1-(methyl-)ethoxy and the like.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge SM, et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with inorganic or organic bases, such as metal bases or amines, such as alkali and alkaline earth metal bases, e.g., hydroxides or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge SM, et al., "Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

For medical use, the amount required of a compound of Formula I or pharmacologically acceptable salt thereof to achieve a therapeutic effect will, of course, vary both with the particular compound, the route of administration, the mammal under treatment, and the particular disorder of disease concerned. A suitable dose of a compound of Formula I or pharmacologically acceptable salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of HIV infections in general, due to any course, a suitable dose of a compound of Formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 mg to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound of Formula I. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, transdermal and transmucosal systems, and capsules can be used as solid dosage forms suitable for oral administration.

Liquid form preparations include solutions, suspensions, and emulsions. As an example, water or water-propylene glycol solutions may be mentioned for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents. Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

Particularly, the present invention is the use of the following compounds in their free form or as pharmaceutically acceptable salts to substantially inhibit HIV or substantially inhibit the activation of HIV in an HIV-infected individual by administering an effective amount in unit dosage form of:

5-methoxy-3-(1-methylethoxy)benzothiophene-2-carboxamide;

3-(1-methylethoxy)benzothiophene-2-carboxamide;

5-chloro-3-(1-methylethoxy)benzothiophene-2-carboxamide;

5-methyl-3-(1-methylethoxy)benzothiophene-2-carboxamide;

3-(1-methylethoxy)-5-nitrobenzothiophene-2-carboxamide;

7-methoxy-3-(1-methylethoxy)benzothiophene-2-carboxamide;

3,5-dimethoxybenzothiophene-2-carboxamide;

5-methoxy-3-(phenylmethoxy)benzothiophene-2-carboxamide;

5-methoxy-3-(phenoxy)benzothiophene-2-carboxamide;

5-hydroxy-3-(1-methylethoxy)benzothiophene-2-carboxamide;

6-methoxy-3-(1-methylethoxy)benzothiophene-2-carboxamide;

4-[[[5-methoxy-3-(1-methylethoxy)benzothien-2-yl]carbonyl]amino]benzoic acid;

3-[[[5-methoxy-3-(1-methylethoxy)benzothien-2-yl]carbonyl]amino]benzoic acid;

ethyl 2-[[[5-methoxy-3-(1-methylethoxy)benzothien-2-yl]carbonyl]amino]benzeneacetate;

2-[[[5-methoxy-3-(1-methylethoxy)benzothien-2-yl]carbonyl]amino]benzoic acid;

4-[[[5-methoxy-3-(1-methylethoxy)benzothien-2-yl]carbonyl]aminomethyl]benzoic acid;

methyl 4-[[[5-methoxy-3-(1-methylethoxy)benzothien-2-yl]carbonyl]amino]benzeneacetate;

4-[[[5-methoxy-3-(1-methylethoxy)benzothien-2-yl]carbonyl]amino]benzeneacetic acid;

methyl 3-[[[5-methoxy-3-(1-methylethoxy)benzothien-2-yl]carbonyl]amino]benzeneacetate;

3-[[[5-methoxy-3-(1-methylethoxy)benzothien-2-yl]carbonyl]amino]benzeneacetic acid;

methyl 5-[[[5-methoxy-3-(1-methylethoxy)benzothien-2-yl]carbonyl]amino]pentanoate;

5-[[[5-methoxy-3-(1-methylethoxy)benzothien-2-yl]carbonyl]amino]pentanoic acid;

3-[[[5-methoxy-3-(1-methylethoxy)benzothien-2-yl]carbonyl]amino-2-thiophenecarboxylic acid;

5-methoxy-N-methyl-(3-(1-methylethoxy)benzothiophene-2-carboxamide;

N-ethyl-(5-methoxy-3-(1-methylethoxy)benzothiophene-2-carboxamide;

5-methoxy-3-(1-methylethoxy)-N-phenylbenzothiophene-2-carboxamide;

5-methoxy-3-(1-methylethoxy)-N-(phenylmethyl)-benzothiophene-2-carboxamide;

5-methoxy-3-(1-methylethoxy)benzothiophene-2-carboxamide-1-oxide;

5-methoxy-3-(1-methylethoxy)benzothiophene-2-carboxamide-1,1'-dioxide;

3-(1,1-dimethylethoxy)-5-methoxybenzothiophene-2-carboxamide;

6-chloro-3-(1-methylethoxy)benzothiophene-2-carboxamide;

5-amino-3-(1-methylethoxy)benzothiophene-2-carboxamide;

methyl 4-[[[5-methoxy-3-(1-methylethoxy)benzothien-2-yl]carbonyl]amino]butanoate;

4-[[[5-methoxy-3-(1-methylethoxy)benzothien-2-yl]carbonyl]amino]butanoic acid; or 5 -methoxy-3-(1-methylethoxy)-N-(1-methylethyl)-benzothiophene-2-carboxamide.

The foregoing compounds of general Formula I can be used in the form of the isomeric mixtures or can optionally be separated by known separation processes, such as crystallization or chromatography. Compounds of general Formula I which have a chiral centre can be used as stereoisomeric mixtures or in the form of the enantiomers. The enantiomers can be obtained by the processes conventionally used for the separation of stereoisomers.

It is indicated that the compounds of the present invention may be used to inhibit HIV or inhibit the activation of HIV in HIV-infected individuals. Preferably, the compounds of the present invention are used to inhibit HIV-1 or the activation of HIV-1 in HIV-infected individuals. Nevertheless, the use of the compounds of the present invention is not limited to treating HIV-1 infections and it should be understood that they may be used to treat HIV-2, HIV-3, HTLV-1, HTLV-2, or HTLV-3 infections, and any other strains of HIV or HTLV whose asymptomatic period would be extended or prolonged by the compounds of the present invention which substantially inhibit HIV or their activation in HIV-infected individuals.

In addition, the compounds may be administered to inhibit HIV in an acute infection as well as a chronic infection. Nevertheless, it is preferred that the compounds be administered to inhibit HIV in an acute infection.

It should further be understood that the present invention is also directed to combinations of the anti-HIV or anti-HIV activating compounds of this invention with one or more agents useful in the treatment of AIDS. For example, the compounds of this invention may be effectively administered in combination with effective amounts of the AIDS antivirals, immunomodulators, anti-infectives, or vaccines known to those of ordinary skill in the art. It will be understood that the scope of combinations of the compounds of this invention with AIDS antivirals, immunomodulators, anti-infectives, or vaccines include in principle any combination with any pharmaceutical composition useful for the treatment of AIDS.

As used herein, the term "latent HIV" or individual infected with HIV in an "asymptomatic" state refers to the integration of human immunodeficiency viral or proviral DNA into host or mammalian genetic material concomitant with periods of substantially no viral expression. The length of time HIV is latent, or an individual is in an asymptomatic state, and non or substantially nonexpressive, varies with respect to such factors as age, gender, or race.

The term "expression" is relative. Complete expression has been defined as the basic scenario whereby HIV transcribes all viral proteins, assembles those proteins at lamellar membrane structures, and presents budding particle. It should be understood that as defined herein, the ability of the compounds of the present invention to prevent or substantially prevent complete expression constitutes the ability of the compounds to prevent or substantially prevent activation of HIV from a stage of nonexpression or latency.

The ability of the compounds of the present invention to prevent or substantially prevent the activation of HIV from a latent state can also be defined with regard to CD4 down modulation, and/or reverse transcriptase determinations, or other markers of HIV activity known to those of skill in the art such as protease activity.

Activation of HIV from a latent stage is associated with down modulation of the CD4 cell marker and increased reverse transcriptase activity for example. Use of the compounds of the present invention to treat HIV-infected cells inhibits or substantially inhibits CD4 down modulation and/or reverse transcriptase activity.

The usefulness of the compounds of the present invention as inhibitors HIV, inhibitors of the activation of latent HIV, as immunosuppressives, or in treating other immune diseases affecting an individual may be demonstrated by their effectiveness in various standard test procedures (see Feorino PM, et al., *Antiviral Chemistry and Chemotherapy* 1993;4(1):55–63 which is incorporated herein by reference). Specifically, the anti-latent HIV activator activity of the compounds having the Formula I of the present invention was determined by taking advantage of the OM-10.1 cell line, described above, a unique chronically-infected promyelocytic clone which remains CD4+ until HIV-1 activation with tumor necrosis factor-$\alpha$ or other cytokines known to those of skill in the art to activate HIV-1.

The following nonlimiting examples illustrate the preferred methods for using the compounds of the invention.

EXAMPLES

The following examples illustrate techniques discovered by the inventors for treating mammals infected with HIV. It should be appreciated by those of skill-in-the-art that the techniques disclosed in the examples which follow represent laboratory techniques discovered by the inventors to function well in the practice of the invention, and thus can be considered to constitute preferred modes for its practice. Those of skill-in-the-art should, however, in light of the present disclosure, appreciate that many changes can be made in the specific embodiments which are disclosed and still obtain a like or similar result without departing from the spirit and scope of the invention. In other words, the following examples are given to illustrate particular compositions and methods within the scope of the present invention and are not intended to limit the scope of the present invention.

EXAMPLE 1

Example 1 was performed as described by Butera ST, et al., *J. Virol.* 1991;65:4645–4653. Test compounds were first dissolved in 100% DMSO to the indicated stock concentrations below in Table I. The stock solution was then diluted in tissue culture starting at 1:100(10−2) and proceeding on as indicated.

TABLE I

| Dilution | Test Compound A[1] | Test Compound B[2] |
| --- | --- | --- |
| [Stock] | 20.0 mM | 35.5 mM |
| 1:2000 | 10.0 μM | 17.75 μM |
| 1:4000 | 5.0 μM | 8.88 μM |
| 1:8000 | 2.5 μM | 4.44 μM |
| 1:16,000 | 1.25 μM | 2.22 μM |
| 1:32,000 | 0.62 μM | 1.11 μM |
| 1:64,000 | 0.31 μM | 0.55 μM |
| 1:128,000 | 0.16 μM | 0.28 μM |
| 1:256,000 | 78.0 nM | 0.14 μM |
| 1:512,000 | 39.0 nM | 70.0 nM |
| 1:10 6 | 19.5 nM | 35.0 nM |

[1]Test Compound A - 5-methoxy-3-(1-methylethoxy)benzo[b]-thiophene-2-carboxamide,
[2]Test Compound B - 5-methoxy-3-(1-methylethoxy)benzo[b]-thiophene-2-carboxamide-, 1-oxide OM-10.1 cells were then pretreated for 4 hours with the test compounds prior to TNF-α induction. TNF-α was added at 20 U/ml and induced cells were examined at 24 hours for evidence of surface CD4 down-modulation, as an indication of viral activation. Cells were also harvested after 24 hours of TNF-α induction for drug toxicity, being labeled with $^3$H thymidine during the final 18 hours in culture. At hours, cell-free culture supernatant was collected for reverse transcriptase determination, as a further verification of the extent of HIV-1 activation. CD4 surface staining for flow cytometry and reverse transcriptase analysis were performed as described.

Two of the compounds, 5-methoxy-3-(1-methylethoxy)benzothiophene-2-carboxamide and 5-methoxy-3-(1-methylethoxy)benzothiophene-2-carboxamide-, 1-oxide, appeared to have anti-induction activity in the OM-10.1 cell system. This was especially true for 5-methoxy-3-(1-methylethoxy)benzothiophene-2-carboxamide-, 1-oxide where concentrations between 10 and 1 μM were effective at substantially inhibiting HIV-1 activation. Higher concentrations (20.0 μM) of the tested compounds appeared to completely inhibit HIV-1 activation. Although host cellular toxicity must be taken into consideration, nearly complete inhibition was also evident by CD4+ analysis. The foregoing results are evidenced by the following Tables II–IV and accompanying FIGS. 1–4.

Table II details the mean reverse transcriptase cpm values obtained from an analysis of the OM-10.1 TNF-α induced cultures with Test Compounds A and B. The values are graphically represented in FIG. 1.

Table III details the percent inhibition of the reverse transcriptase activity of OM-10.1 TNF-α induced cultures with Test Compounds A and B. The values are graphically represented in FIG. 2.

Table IV details the stimulation index (SI) value of the reverse transcriptase activity of OM-10.1 TNF-α induced cultures with Test Compounds A and B. The SI value is a measure of activity that compares a TNF-α treated culture to a non-TNF-α treated medium culture for incorporation of radio labeled nucleotides by reverse transcriptase. The values are graphically represented in FIG. 3.

Figure 1:
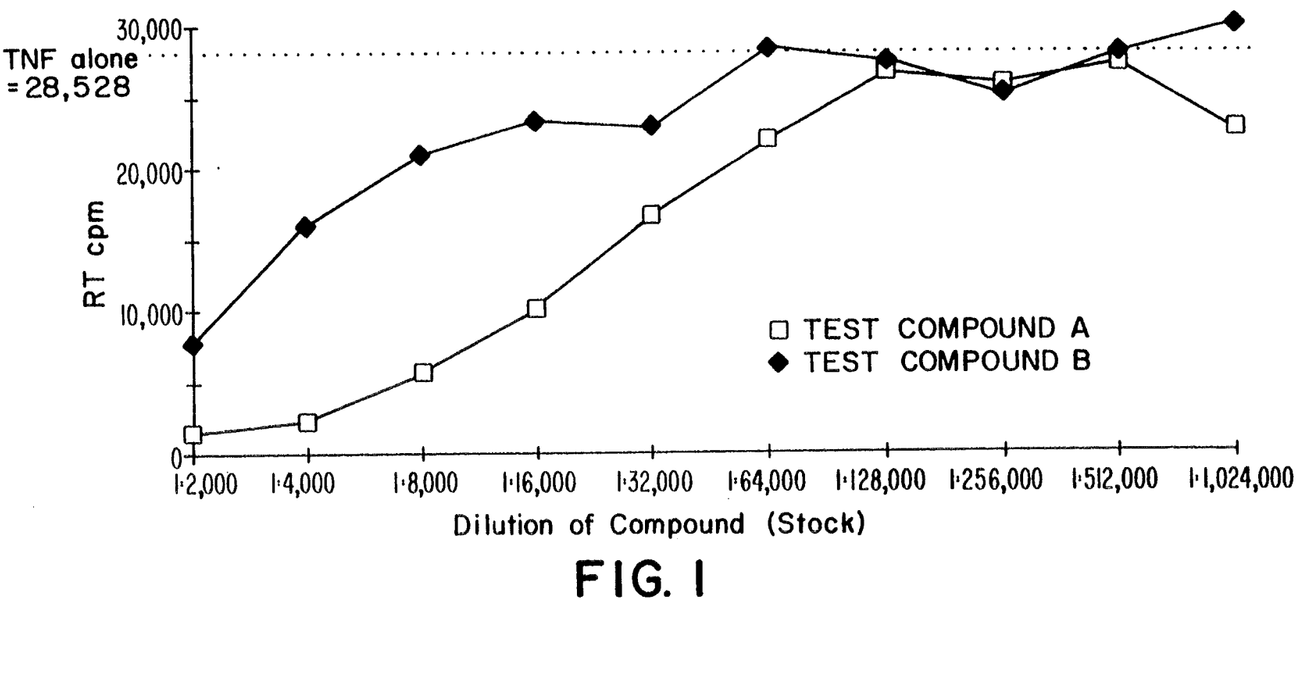
Figure 2:
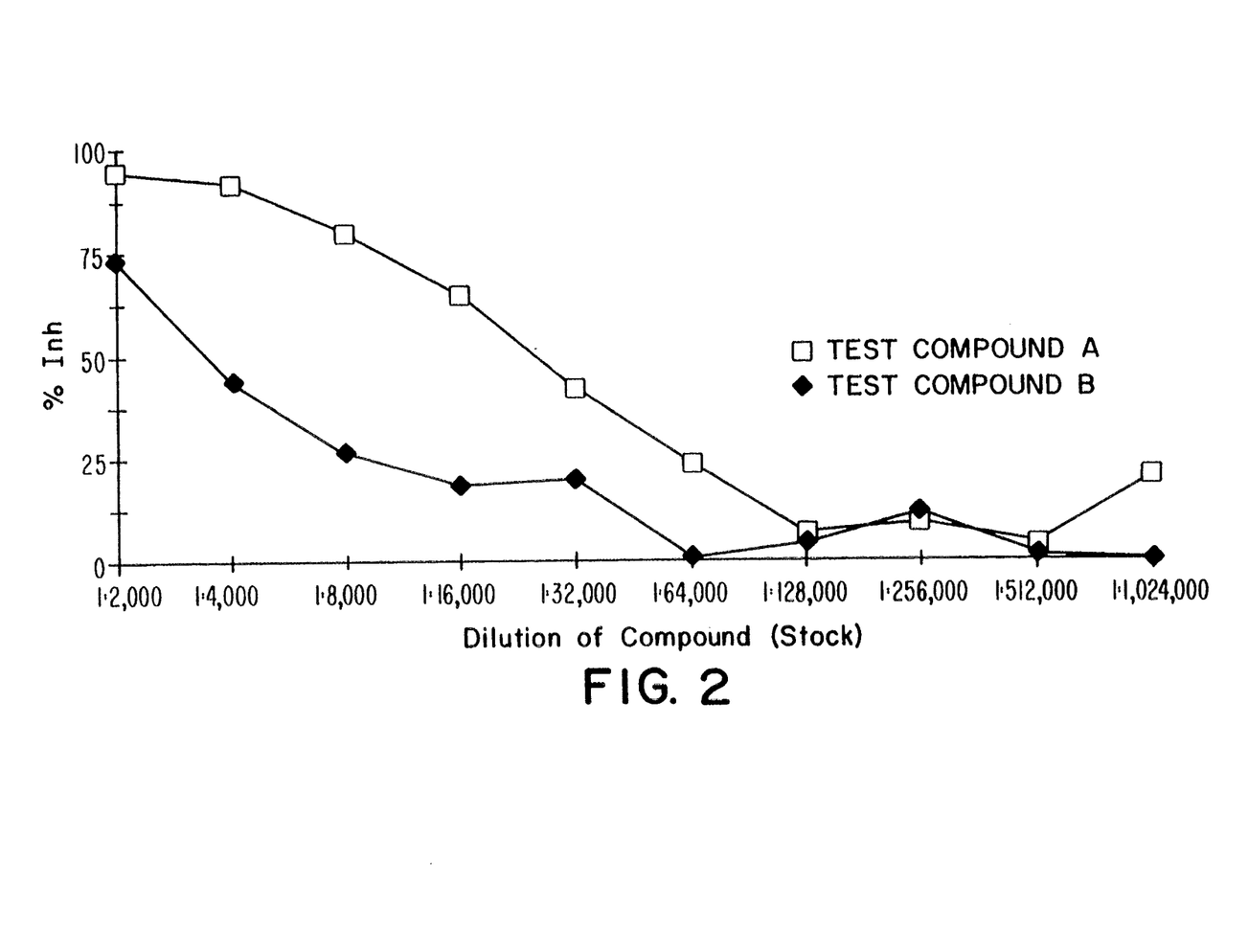
Figure 3:
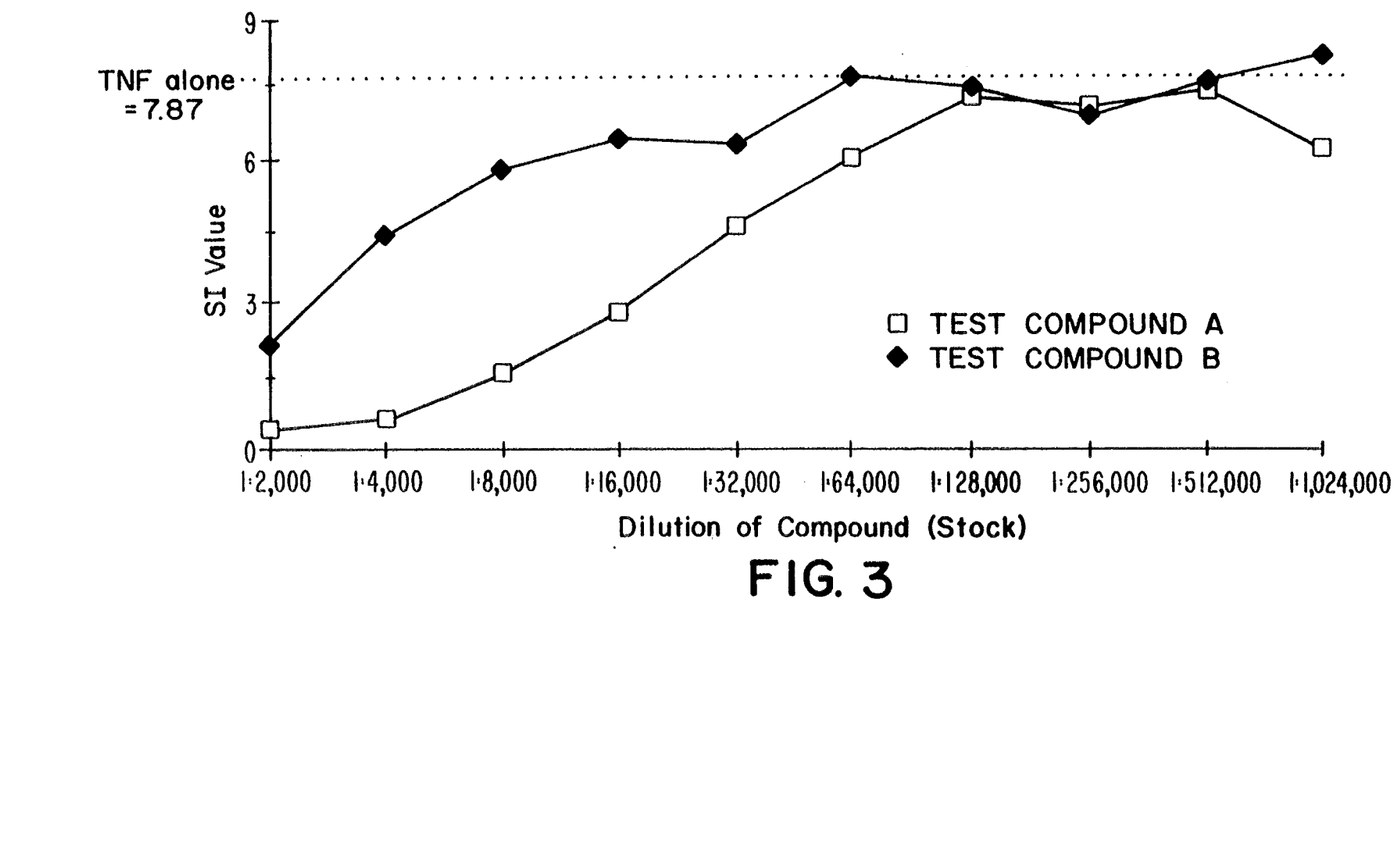
Figure 4:
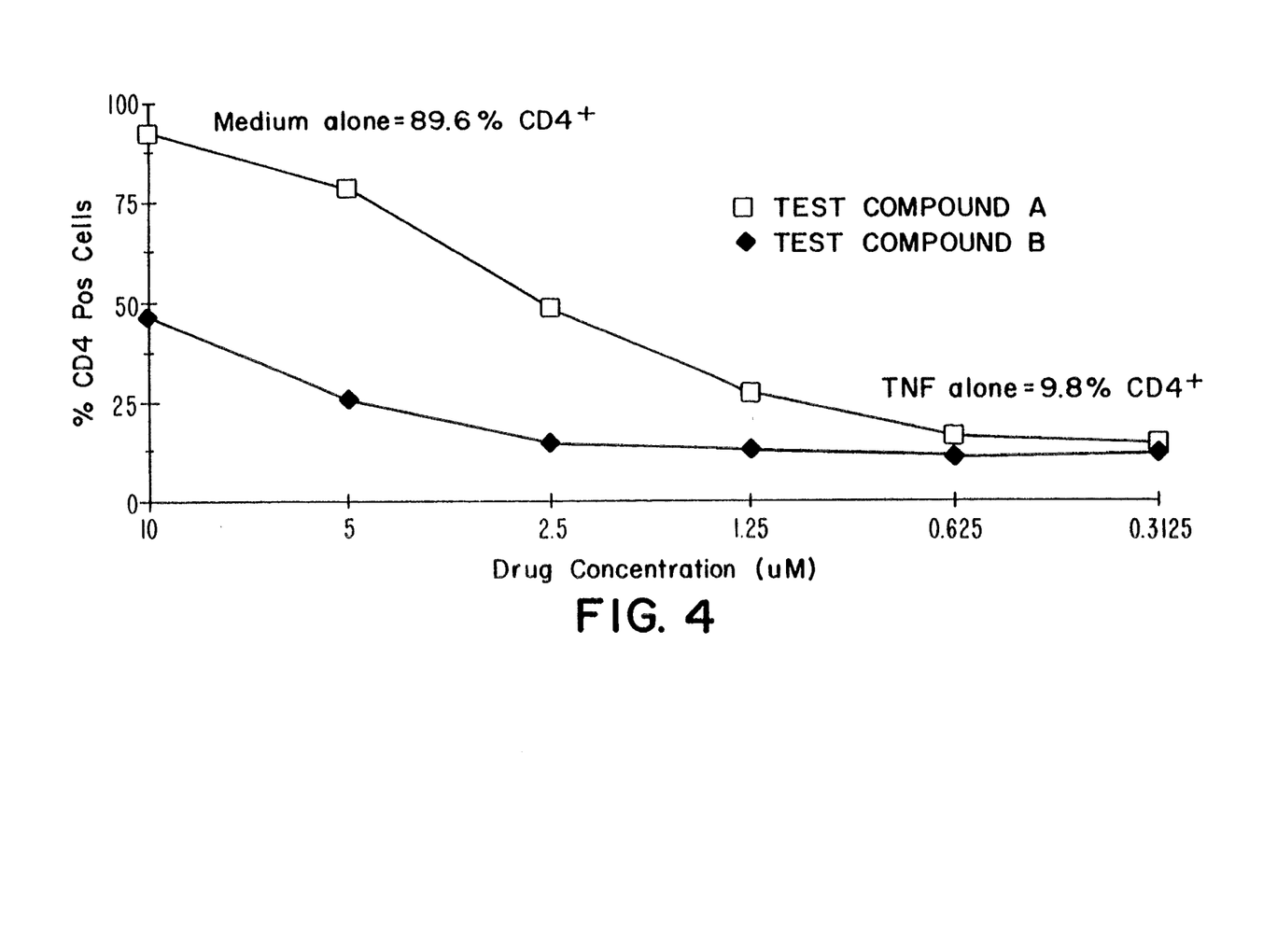

FIG. 4 is a graph representing the inhibition of CD4 down modulation in the OM-10.1 TNF-α induced cultures with Test Compounds A and B. The graph considers the percent of CD4-positive cells at various different concentrations of the test compounds.

TABLE II

| Dilution | Test Compound A | Test Compound B | TNF | Medium |
| --- | --- | --- | --- | --- |
| 1:2000 | 1,494 | 7,725 | 28,528 | 3625 |
| 1:4000 | 2,322 | 15,984 | | |
| 1:8000 | 5,766 | 21,009 | | |
| 1:16,000 | 10,103 | 23,336 | | |
| 1:32,000 | 16,673 | 22,931 | | |
| 1:64,000 | 21,941 | 28,334 | | |
| 1:128,000 | 26,642 | 27,480 | | |
| 1:256,000 | 25,905 | 25,257 | | |
| 1:512,000 | 27,334 | 28,085 | | |
| 1:10 6 | 24,994 | 30,025 | | |

TABLE III

| Dilution | Test Compound A | Test Compound B |
| --- | --- | --- |
| 1:2000 | 94.76 | 72.92 |
| 1:4000 | 91.86 | 43.97 |
| 1:8000 | 79.79 | 26.36 |
| 1:16,000 | 64.59 | 18.20 |
| 1:32,000 | 41.56 | 19.62 |
| 1:64,000 | 23.09 | 0.68 |
| 1:128,000 | 6.61 | 3.67 |
| 1:256,000 | 9.19 | 11.47 |
| 1:512,000 | 4.19 | 1.55 |
| 1:10 6 | 12.39 | 0.00 |

TABLE IV

| Dilution | Test Compound A | Test Compound B | TNF |
| --- | --- | --- | --- |
| 1:2000 | 0.41 | 2.13 | 7.87 |
| 1:4000 | 0.64 | 4.41 | |
| 1:8000 | 1.59 | 5.80 | |
| 1:16,000 | 2.79 | 6.44 | |
| 1:32,000 | 4.60 | 6.33 | |
| 1:64,000 | 6.05 | 7.82 | |
| 1:128,000 | 7.35 | 7.58 | |
| 1:256,000 | 7.15 | 6.97 | |
| 1:512,000 | 7.54 | 7.75 | |
| 1:10 6 | 6.89 | 8.28 | |

EXAMPLE 2

Example 2 was conducted in a manner similar to Example 1. Unlike Example 1, however, OM-10.1 cells were pretreated for 24 hours with TNF-α, prior to the addition of the test compounds 5-methoxy-3-(1-methylethoxy) benzothiophene-2-carboxamide (A) and 5-methoxy-3-(1-methylethoxy)benzothiophene-2-carboxamide-, 1-oxide (B). Moreover, in Example 2 the experiment was extended through 96 hours after the removal of TNF-α. The results of Example 2 with respect to Test Compound A are shown below in Table V, reported in terms of percent CD4-positive cells, and illustrated graphically in FIG. 5. The results of Example 2 with respect to Test Compound B are shown below in Table XI, reported in terms of percent CD4-positive cells, and illustrated graphically in FIG. 6.

TABLE V

|  | T-24 | T-0 | 24 | 48 | 72 | 96 |
| --- | --- | --- | --- | --- | --- | --- |
| Medium | 89.0 | 4.0 | 4.6 | 16.4 | 39.5 | 62.6 |
| 10 μM | 89.0 | 4.0 | 10.8 | 76.4 | 87.2 | 98.0 |
| 2.5 μM | 89.0 | 4.0 | 31.4 | 96.1 | 97.1 | 98.0 |
| 0.5 μM | 89.0 | 4.0 | 6.9 | 42.8 | 68.0 | 93.1 |
| TNF | 89.0 | 4.0 | 2.4 | 5.0 | 7.4 | 9.7 |

TABLE VI

|  | T-24 | T-0 | 24 | 48 | 72 | 96 |
| --- | --- | --- | --- | --- | --- | --- |
| Medium | 89.0 | 4.0 | 4.6 | 16.4 | 39.5 | 62.6 |
| 10 μM | 89.0 | 4.0 | 33.5 | 96.5 | 97.6 | 98.7 |
| 2.5 μM | 89.0 | 4.0 | 10.9 | 57.3 | 76.6 | 95.9 |
| 0.5 μM | 89.0 | 4.0 | 5.3 | 20.6 | 47.9 | 75.1 |
| TNF | 89.0 | 4.0 | 2.4 | 5.0 | 7.4 | 9.7 |

Figure 5:
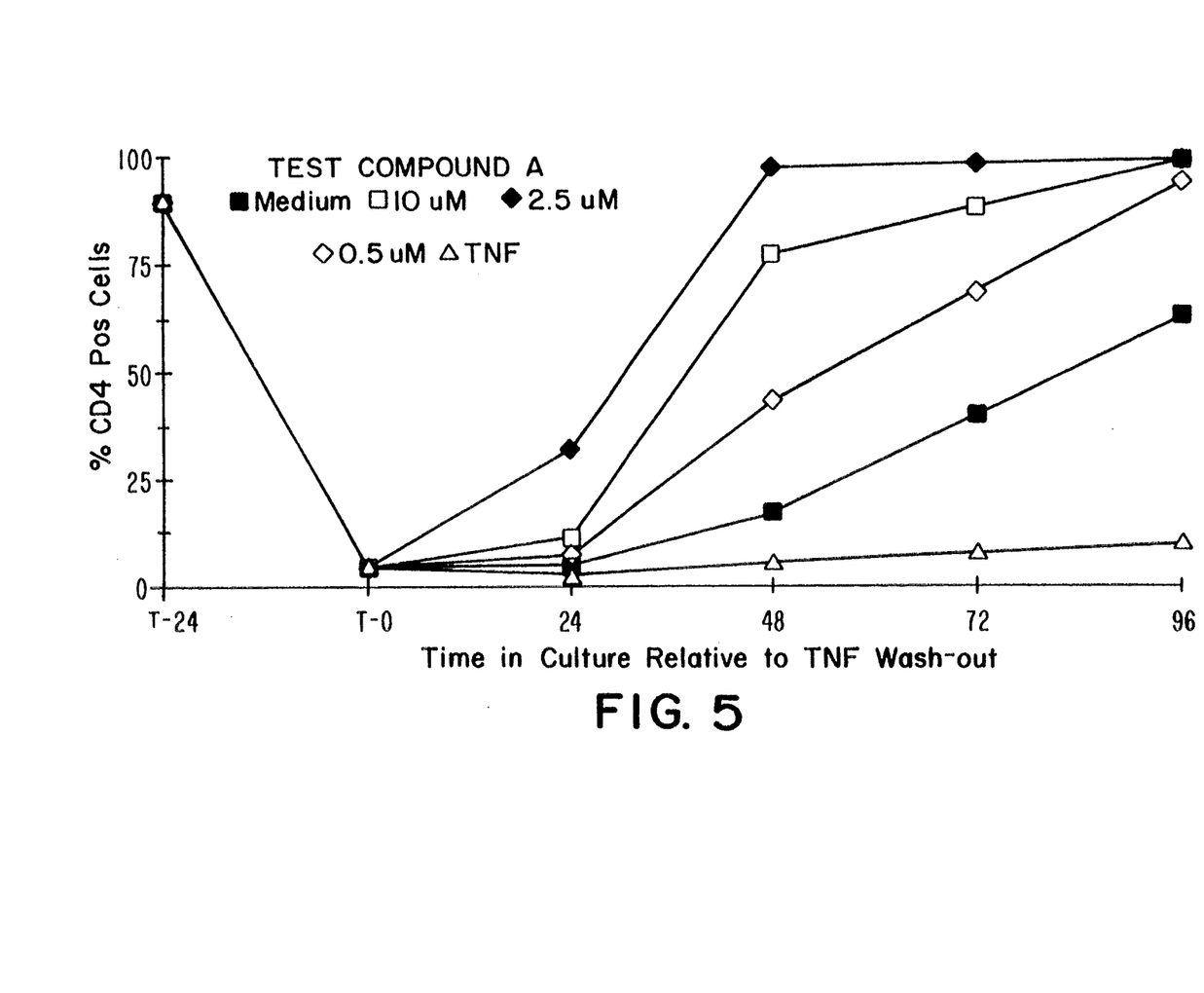
FIG. 5 is a graph representing the return to a latent state of the OM-10.1 cultures treated with 5-methoxy-3-(1-methylethoxy)benzothiophene-2-carboxamide.
Figure 6:
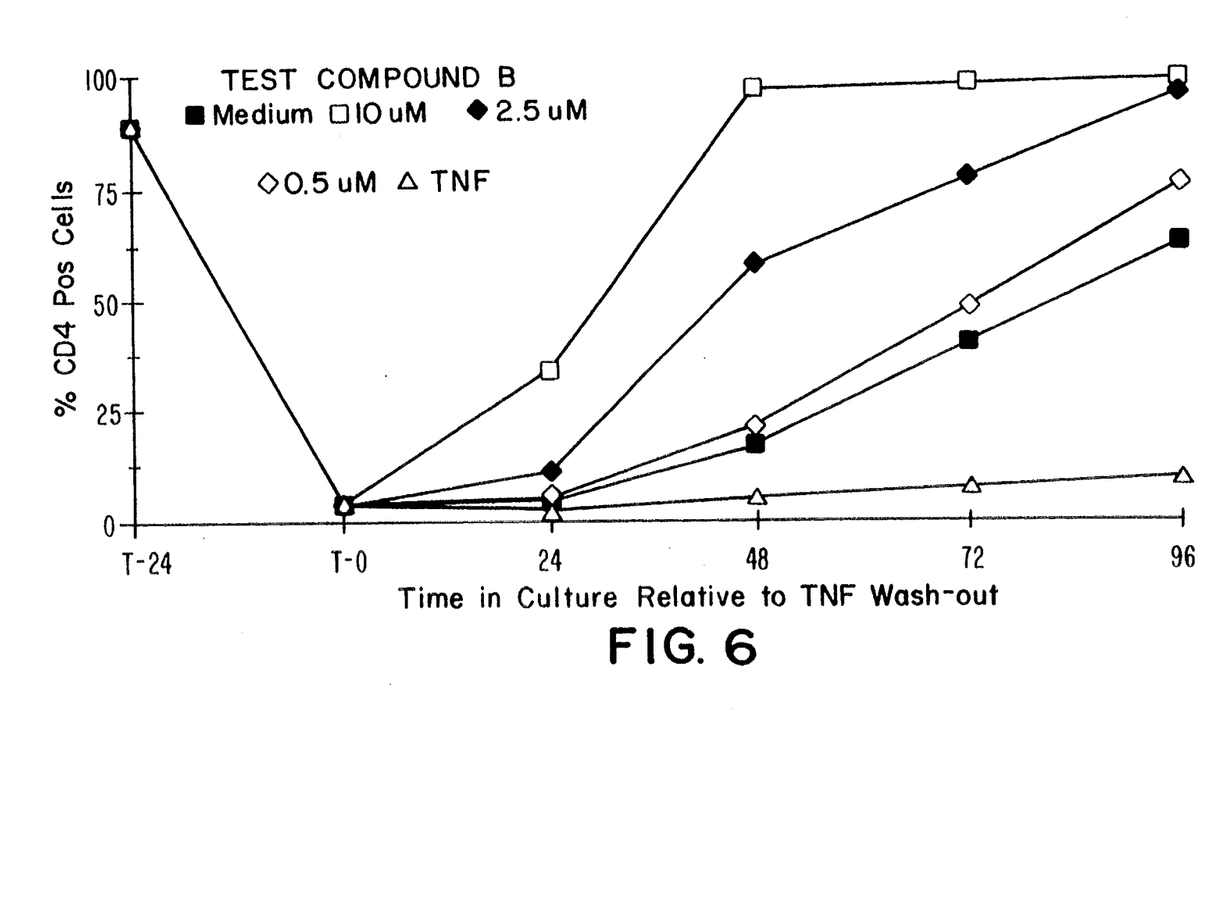
FIG. 6 is a graph representing the return to a latent state of the OM-10.1 cultures treated with 5-methoxy-3-(1-methylethoxy)benzothiophene-2-carboxamide-, 1-oxide.

AS illustrated in FIGS. 5 and 6, treatment with the test compounds to TNF-α stimulated OM-10.1 cells quickly returned activated HIV-1 to a state of latency. At 48 hours, the return to latency induced by the test compounds was significant. The pattern did not change through 96 hours except that the medium culture continued to return to latency. The return to latency was evidenced by an accelerated return of surface CD4, and the data for FIGS. 5 and 6 was generated in terms of percent CD4-positive cells by flow cytometry.

EXAMPLE 3

Antiviral assays of acute HIV-1 infection were performed in H9 and MT-4 cell lines. Cultures were batch infected in 1 mL of RPMI 1640 media/10% fetal calf serum containing $10^7$ cells and $10^5$ infectious doses of HIV-1$_{iiib}$; for an effective multiplicity of infection of 0.01. After 2 hours of viral absorption, cells were washed once and plated in 96-well microtiter plates at a density of $10^4$ cells per well. The test compound, 5-methoxy-3-(1-methylethoxy)benzothiophene-2-carboxamide, was added to produce the desired concentration of drug and 0.2% DMSO in a final volume of 200 μL. Cultures were tested for inhibition of reverse transcriptase activity to evidence reversal of HIV-1 induction by a reverse transcriptase assay at 7 days postinfection. Results of the reverse transcriptase assay are listed below in Table XIII and reported in terms of IC$_{50}$ and TC$_{50}$ values.

TABLE XII

| μM | MT-4 | H9 |
| --- | --- | --- |
| IC$_{50}$ | 0.1 | 0.9 |
| TC$_{50}$ | 6.3 | 2.5 |

A detailed description of the drug preparation and dilution, plate format, XTT assay, reverse transcriptase assay, and data analysis can be found by reference to the protocol provided in *J. Virol* 1991;65:4645–4653. Additional references are as follows:

Harada S, Koyanagi Y, Yamamoto N. Infection of HTLV-III/LAV in HTLV-1 carrying cells MT-2 and MT-4 and application in a plaque assay. *Science* 1985;229:563–566.

Pauwels R, DeClercq E, Desmyter, et al. Sensitive and rapid assay on MT-4 cells on MT-4 cells for detection of antiviral compounds against the AIDS virus. *J. Virol. Methods* 1987;16:171–185.

Mann D, O'Brien S, Gilbert D, et al. Origin of the HIV-susceptible human CD4+ cell line H9. AIDS Research and Human Retroviruses %: 1989;253–255.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for substantially inhibiting HIV or the activation of HIV in an HIV-infected individual which comprises administering a therapeutically effective amount of a compound of the following formula:

wherein
R$_1$ is lower alkyl, phenyl, or benzyl;
R$_2$ is hydrogen, lower alkyl, phenyl, benzyl, thiophene, (CH$_2$)$_m$Q, or phenyl, benzyl, or thiophene substituted with (CH$_2$)$_m$Q;
n is an integer from 0 to 2;
m is an integer from 0 to 6;
Q is CO$_2$R$_7$ where R$_7$ is hydrogen or lower alkyl; and
R$_3$, R$_4$, R$_5$, R$_6$ are independently hydrogen, halo, hydroxy, nitro, amino, lower alkyl, and lower alkoxy
as well as of the pharmaceutically acceptable salts of compounds of Formula I.

2. The method as defined in claim 1, wherein the method is for substantially inhibiting HIV-1 or the activation of HIV-1.

3. The method as defined in claim 1 where the compound is:
5-hydroxy-3-(1-methylethoxy)benzothiophene-2-carboxamide.

4. The method as defined in claim 1 where the compound is:
5-methoxy-3-(1-methylethoxy)benzothiophene-2-carboxamide.

5. The method as defined in claim 1 where the compound is:
5-methoxy-3-(1-methylethoxy)benzothiophene-2-carboxamide-, 1-oxide.

6. The method as defined in claim 1 where the compound is:
3-(1-methylethoxy)benzothiophene-2-carboxamide;
5-chloro-3-(1-methylethoxy)benzothiophene-2-carboxamide;
5-methyl-3-(1-methylethoxy)benzothiophene-2-carboxamide;
3-(1-methylethoxy)-5-nitrobenzothiophene-2-carboxamide;
7-methoxy-3-(1-methylethoxy)benzothiophene-2-carboxamide;
3,5-dimethoxybenzothiophene-2-carboxamide;
5-methoxy-3-(phenylmethoxy)benzothiophene-2-carboxamide;
5-methoxy-3-(phenoxy)benzothiophene-2-carboxamide;

6-methoxy-3-(1-methylethoxy)benzothiophene-2-carboxamide;
4-[[[5-methoxy-3-(1-methylethoxy)benzothien-2-yl]carbonyl]amino]benzoic acid;
3-[[[5-methoxy-3-(1-methylethoxy)benzothien-2-yl]carbonyl]amino]benzoic acid;
ethyl 2-[[[5-methoxy-3-(1-methylethoxy)benzothien-2-yl]carbonyl]amino]benzeneacetate;
2-[[[5-methoxy-3-(1-methylethoxy)benzothien-2-yl]carbonyl]amino]benzoic acid;
4-[[[5-methoxy-3-(1-methylethoxy)benzothien-2-yl]carbonyl]aminomethyl]benzoic acid;
methyl 4-[[[5-methoxy-3-(1-methylethoxy)benzothien-2-yl]carbonyl]amino]benzeneacetate;
4-[[[5-methoxy-3-(1-methylethoxy)benzothien-2-yl]carbonyl]amino]benzeneacetic acid;
methyl 3-[[[5-methoxy-3-(1-methylethoxy)benzothien-2-yl]carbonyl]amino]benzeneacetate;
3-[[[5-methoxy-3-(1-methylethoxy)benzothien-2-yl]carbonyl]amino]benzeneacetic acid;
methyl 5-[[[5-methoxy-3-(1-methylethoxy)benzothien-2-yl]carbonyl]amino]pentanoate;
5-[[[5-methoxy-3-(1-methylethoxy)benzothien-2-yl]carbonyl]amino]pentanoic acid;
3-[[[5-methoxy-3-(1-methylethoxy)benzothien-2-yl]carbonyl]amino-2-thiophenecarboxylic acid;
5-methoxy-N-methyl-(3-(1-methylethoxy)benzothiophene-2-carboxamide;
N-ethyl-(5-methoxy-3-(1-methylethoxy)benzothiophene-2-carboxamide;
5-methoxy-3-(1-methylethoxy)-N-phenylbenzothiophene-2-carboxamide;
5-methoxy-3-(1-methylethoxy)-N-(phenylmethyl)-benzothiophene-2-carboxamide;
5-methoxy-3-(1-methylethoxy)benzothiophene-2-carboxamide 1,1'-dioxide;
3-(1,1-dimethylethoxy)-5-methoxybenzothiophene-2-carboxamide;
6-chloro-3-(1-methylethoxy)benzothiophene-2-carboxamide;
5-amino-3-(1-methylethoxy)benzothiophene-2-carboxamide;
methyl 4-[[[5-methoxy-3-(1-methylethoxy)benzothien-2-yl]carbonyl]amino]butanoate;
4-[[[5-methoxy-3-(1-methylethoxy)benzothien-2-yl]carbonyl]amino]butanoic acid; or
5-methoxy-3-(1-methylethoxy)-N-(1-methylethyl)-benzothiophene-2-carboxamide.

7. The method as defined in claim 1 wherein the compound is administered to an HIV-infected individual along with a pharmaceutically acceptable carrier.

8. A method for substantially inhibiting the activation of HIV in an HIV-infected individual which comprises administering a therapeutically effective amount of a compound of the following Formula:

I wherein
R$_1$ is lower alkyl, phenyl, or benzyl;

R$_2$ is hydrogen, lower alkyl, phenyl, benzyl, thiophene, (CH$_2$)$_m$Q, or phenyl, benzyl, or thiophene substituted with (CH$_2$)$_m$Q;
n is an integer from 0 to 2;
m is an integer from 0 to 6;
Q is CO$_2$R$_7$ where R$_7$ is hydrogen or lower alkyl; and
R$_3$, R$_4$, R$_5$, R$_6$ are independently hydrogen, halo, hydroxy, nitro, amino, lower alkyl, and lower alkoxy
as well as of the pharmaceutically acceptable salts of compounds of Formula I.

9. A method as defined in claim 8 wherein the method is for substantially inhibiting the activation of HIV-1.

10. The method as defined in claim 8 where the compound is:
5-methoxy-3-(1-methylethoxy)benzothiophene-2-carboxamide.

11. The method as defined in claim 8 where the compound is:
5-methoxy-3-(1-methylethoxy)benzothiophene-2-carboxamide-, 1-oxide.

12. The method as defined in claim 8 where the compound is:
5-hydroxy-3-(1-methylethoxy)benzothiophene-2-carboxamide.

13. The method as defined in claim 8 where the compound is:
3-(1-methylethoxy)benzothiophene-2-carboxamide;
5-chloro-3-(1-methylethoxy)benzothiophene-2-carboxamide;
5-methyl-3-(1-methylethoxy)benzothiophene-2-carboxamide;
3-(1-methylethoxy)-5-nitrobenzothiophene-2-carboxamide;
7-methoxy-3-(1-methylethoxy)benzothiophene-2-carboxamide;
3,5-dimethoxybenzothiophene-2-carboxamide;
5-methoxy-3-(phenylmethoxy)benzothiophene-2-carboxamide;
5-methoxy-3-(phenoxy)benzothiophene-2-carboxamide;
6-methoxy-3-(1-methylethoxy)benzothiophene-2-carboxamide;
4-[[[5-methoxy-3-(1-methylethoxy)benzothien-2-yl]carbonyl]amino]benzoic acid;
3-[[[5-methoxy-3-(1-methylethoxy)benzothien-2-yl]carbonyl]amino]benzoic acid;
ethyl 2-[[[5-methoxy-3-(1-methylethoxy)benzothien-2-yl ]carbonyl]amino]benzeneacetate;
2-[[[5-methoxy-3-(1-methylethoxy)benzothien-2-yl]carbonyl]amino]benzoic acid;
4-[[[5-methoxy-3-(1-methylethoxy)benzothien-2-yl]carbonyl]aminomethyl]benzoic acid;
methyl 4-[[[5-methoxy-3-(1-methylethoxy)benzothien-2-yl]carbonyl]amino]benzeneacetate;
4-[[[5-methoxy-3-(1-methylethoxy)benzothien-2-yl benzeneacetic acid;
methyl 3-[[[5-methoxy-3-(1-methylethoxy)benzothien-2-yl]carbonyl]amino]benzeneacetate;
3-[[[5-methoxy-3-(1-methylethoxy)benzothien-2-yl]carbonyl]amino]benzeneacetic acid;
methyl 5-[[[5-methoxy-3-(1-methylethoxy)benzothien-2-yl]carbonyl]amino]pentanoate;
5-[[[5-methoxy-3-(1-methylethoxy)benzothien-2-yl]carbonyl]amino]pentanoic acid;
3-[[[5-methoxy-3-(1-methylethoxy)benzothien-2-yl]carbonyl]amino-2-thiophenecarboxylic acid;

5-methoxy-N-methyl-(3-(1-methylethoxy)benzothiophene-2-carboxamide;
N-ethyl-(5-methoxy-3-(1-methylethoxy)benzothiophene-2-carboxamide;
5-methoxy-3-(1-methylethoxy)-N-phenyl-benzothiophene-2-carboxamide;
5-methoxy-3-(1-methylethoxy)-N-(phenyl-methyl)-benzothiophene-2-carboxamide;
5-methoxy-3-(1-methylethoxy)benzothiophene2-carboxamide 1,1'-dioxide;
3-(1,1-dimethylethoxy)-5-methoxybenzothiophene-2-carboxamide;
6-chloro-3-(1-methylethoxy)benzothiophene-2-carboxamide;
5-amino-3-(1-methylethoxy)benzothiophene-2-carboxamide;
methyl 4-[[[5-methoxy-3-(1-methylethoxy)benzothien-2-yl]carbonyl]amino]butanoate;
4-[[[5-methoxy-3-(1-methylethoxy)benzothien-2-yl]carbonyl]amino]butanoic acid; or
5-methoxy-3-(1-methylethoxy)-N-(1-methylethyl)-benzothiophene-2-carboxamide.

14. The method as defined in claim 8 wherein the compound is administered to an infected individual along with a pharmaceutically acceptable carrier.

15. A method for substantially inhibiting HIV in an acute HIV-infected individual which comprises administering a therapeutically effective amount of a compound of the following Formula:

wherein
$R_1$ is lower alkyl, phenyl, or benzyl;
$R_2$ is hydrogen, lower alkyl, phenyl, benzyl, thiophene, $(CH_2)_mQ$, or phenyl, benzyl, thiophene substituted with $(CH_2)_mQ$;
n is an integer from 0 to 2;
m is an integer from 0 to 6;
Q is $CO_2R_7$ where $R_7$ is hydrogen or lower alkyl; and
$R_3$, $R_4$, $R_5$, $R_6$ are independently hydrogen, halo, hydroxy, nitro, amino, lower alkyl, and lower alkoxy alkyl, and lower alkoxy as well as of the pharmaceutically acceptable salts of compounds of Formula I.

16. A method as defined in claim 15 wherein the method is for substantially inhibiting the activation of HIV-1.

17. The method as defined in claim 15 where the compound is:
5-methoxy-3-(1-methylethoxy)benzothiophene-2-carboxamide.

18. The method as defined in claim 15 where the compound is:
5-methoxy-3-(1-methylethoxy)benzothiophene-2-carboxamide-, 1-oxide.

19. The method as defined in claim 15 where the compound is:
5-hydroxy-3-(1-methylethoxy)benzothiophene-2-carboxamide.

20. The method as defined in claim 15 where the compound is:
3-(1-methylethoxy)benzothiophene-2-carboxamide;
5-chloro-3-(1-methylethoxy)benzothiophene-2-carboxamide;
5-methyl-3-(1-methylethoxy)benzothiophene-2-carboxamide;
3-(1-methylethoxy)-5-nitrobenzothiophene-2-carboxamide;
7-methoxy-3-(1-methylethoxy)benzothiophene-2-carboxamide;
3,5-dimethoxybenzothiophene-2-carboxamide;
5-methoxy-3-(phenylmethoxy)benzothiophene-2-carboxamide;
5-methoxy-3-(phenoxy)benzothiophene-2-carboxamide;
6-methoxy-3-(1-methylethoxy)benzothiophene-2-carboxamide;
4-[[[5-methoxy-3-(1-methylethoxy)benzothien-2-yl]carbonyl]amino]benzoic acid;
3-[[[5-methoxy-3-(1-methylethoxy)benzothien-2-yl]carbonyl]amino]benzoic acid;
ethyl 2-[[[5-methoxy-3-(1-methylethoxy)benzothien-2-yl]carbonyl]amino]benzeneacetate;
2-[[[5-methoxy-3-(1-methylethoxy)benzothien-2-yl]carbonyl]amino]benzoic acid;
4-[[[5-methoxy-3-(1-methylethoxy)benzothien-2-yl]carbonyl]aminomethyl]benzoic acid;
methyl 4-[[[5-methoxy-3-(1-methylethoxy)benzothien-2-yl]carbonyl]amino]benzeneacetate;
4-[[[5-methoxy-3-(1-methylethoxy)benzothien-2-yl]carbonyl]amino]benzeneacetic acid;
methyl 3-[[[5-methoxy-3-(1-methylethoxy)benzothien-2-yl]carbonyl]amino]benzeneacetate;
3-[[[5-methoxy-3-(1-methylethoxy)benzothien-2-yl]carbonyl]amino]benzeneacetic acid;
methyl 5-[[[5-methoxy-3-(1-methylethoxy)benzothien-2-yl]carbonyl]amino]pentanoate;
5-[[[5-methoxy-3-(1-methylethoxy)benzothien-2-yl]carbonyl]amino]pentanoic acid;
3-[[[5-methoxy-3-(1-methylethoxy)benzothien-2-yl]carbonyl]amino-2-thiophenecarboxylic acid;
5-methoxy-N-methyl-(3-(1-methylethoxy)benzothiophene-2-carboxamide;
N-ethyl-(5-methoxy-3-(1-methylethoxy)benzothiophene-2-carboxamide;
5-methoxy-3-(1-methylethoxy)-N-phenyl)benzothiophene-2-carboxamide;
5-methoxy-3-(1-methylethoxy)-N-(phenylmethyl)-benzothiophene-2-carboxamide;
5-methoxy-3-(1-methylethoxy)benzothiophene-2-carboxamide 1,1'-dioxide;
3-(1,1-dimethylethoxy)-5-methoxybenzothiophene-2-carboxamide;
6-chloro-3-(1-methylethoxy)benzothiophene-2-carboxamide;
5-amino-3-(1-methylethoxy)benzothiophene-2-carboxamide;
methyl 4-[[[5-methoxy-3-(1-methylethoxy)benzothien-2-yl]carbonyl]amino]butanoate;
4-[[[5-methoxy-3-(1-methylethoxy)benzothien-2-yl]carbonyl]amino]butanoic acid; or
5-methoxy-3-(1-methylethoxy)-N-(1-methylethyl)-benzothiophene-2-carboxamide.

21. The method as defined in claim 15 wherein the compound is administered to an infected individual along with a pharmaceutically acceptable carrier.

* * * * *